United States Patent [19]

Schwartz

[11] Patent Number: 5,330,507
[45] Date of Patent: Jul. 19, 1994

[54] IMPLANTABLE ELECTRICAL VAGAL STIMULATION FOR PREVENTION OR INTERRUPTION OF LIFE THREATENING ARRHYTHMIAS

[75] Inventor: Peter J. Schwartz, Milan, Italy

[73] Assignee: Medtronic, Inc., Minneapolis, Minn.

[21] Appl. No.: 873,437

[22] Filed: Apr. 24, 1992

[51] Int. Cl.$^5$ .............................................. A61N 1/368
[52] U.S. Cl. ..................................... 607/14; 128/705; 128/708; 128/697
[58] Field of Search ........ 128/419 PG, 419 P, 419 D, 128/705, 703, 702, 697, 708; 607/9, 14, 15

[56] References Cited

U.S. PATENT DOCUMENTS

| | | | |
|---|---|---|---|
| 3,421,511 | 1/1969 | Schwartz et al. | 128/418 |
| 3,522,811 | 8/1970 | Schwartz et al. | 128/419 |
| 4,548,209 | 10/1985 | Wielders et al. | 128/419 |
| 4,951,667 | 8/1990 | Markowitz et al. | 128/419 |
| 5,014,698 | 5/1991 | Cohen | 128/419 PG |
| 5,023,326 | 4/1993 | Collins | 128/419 PG |
| 5,107,850 | 4/1992 | Olive | 128/705 |
| 5,135,004 | 8/1992 | Adams et al. | 128/696 |
| 5,154,170 | 10/1992 | Bennett et al. | 128/419 |

OTHER PUBLICATIONS

Bilgutay, et al. "Vagal Tuning" from Journal of Thoracic Cardiovascular Surgery, vol. 56, No. 1, Jul. 1968, pp. 71–82.
Brunwald, et al., "Carotid Sinus Nerve Stimulation in the Treatment of Angina Pectoris and Supraventricular Tachycardia", California Medicine, 112:41–50, Mar. 1970.

Primary Examiner—William E. Kamm
Assistant Examiner—George Manuel
Attorney, Agent, or Firm—Harold R. Patton; John A. Rissman

[57] ABSTRACT

A method and apparatus for stimulating the right or left vagus nerve with continuous and/or phasic electrical pulses, the latter in a specific relationship with the R-wave of the patient's electrogram. The automatic detection of the need for vagal stimulation is responsive to increases in the heart rate greater than a predetermined threshold, the occurrence of frequent or complex ventricular arrhythmias, and/or a change in the ST segment elevation greater than a predetermined or programmed threshold. The system is described with a microprocessor driven, brady therapy device with programming and telemetry capabilities for recording in memory the aforementioned stimulation triggering indicia, including electrogram segments for periods of time preceding and following each instance of vagal stimulation for telemetry out on command.

10 Claims, 3 Drawing Sheets

IMPLANTABLE ELECTRICAL VAGAL STIMULATION FOR PREVENTION OR INTERRUPTION OF LIFE THREATENING ARRHYTHMIAS

BACKGROUND OF THE INVENTION

1. Field of the Invention

This invention relates to a method and apparatus for electrically stimulating the vagal nerves for the prevention of life threatening arrhythmias, either automatically or upon external command by the patient or physician.

2. Description of the Prior Art

Vagal stimulation for the treatment of supraventricular arrhythmias, angina pectoris, and heart failure with an automatic, permanently implantable, medical device has been reported in the literature at least as far back as the early 1960's. The paper "Vagal Tuning" by Bilgutay et al. in the *Journal of Thoracic and Cardiovascular Surgery*, Vol. 56, No. 1, July 1968, pp 71-82 described the concepts of vagal stimulation in the treatment of supraventricular arrhythmias, angina pectoris, and heart failure employing an implantable vagal stimulator. Vagal stimulation was effected through the application of electrical stimulation to the vagus nerve by silastic coated, bipolar electrodes (of the type disclosed in Medtronic U.S. Pat. No. 3,421,511) surgically placed around the intact nerve or nerves. Bilgutay et al. designed and employed three different models of vagal stimulators, the first one having a magnetic switch by which it could be turned on or off from outside the body to study the effects of long term stimulation, the second type also implantable but powered from outside by induction using rf frequency, and the third, external type triggered by the R-wave of the subject's electrocardiogram to provide stimulation only upon an achievement of a certain heart rate. Bilgutay et al. found that when a pulsatile current with a frequency of ten pulses per second and 0.2 milliseconds pulse duration was applied to the vagus nerve, long term effective stimulation could be achieved, and also found that by increasing only the voltage amplitude and current, more predictable changes on the electrocardiogram could be obtained. The heart rate could be decreased down to half the resting rate while still preserving sinus rhythm up to 9 volts applied voltage. Atrial-Ventricular (AV) conduction dissociation and third degree heart block resulted at amplitudes exceeding 9 volts, and complete asystole with vagal escape resulted when the applied voltage exceeded 20 volts. Low amplitude vagal stimulation was successfully employed to control induced tachycardias and ectopic beats, and the authors noted other advantages of vagal stimulation in alleviating adverse effects of available drug therapies.

Other investigators reported treatment of angina pectoris and paroxysmal atrial ventricular junctional or supraventricular tachycardias through application of carotid sinus nerve stimulation employing the Medtronic Angistat carotid sinus nerve stimulator (csns) then available from Medtronic, Inc. in papers such as "Carotid Sinus Nerve Stimulation in the Treatment of Angina Pectoris and Supraventricular Tachycardia", *California Medicine*, 112:41-50, March, 1970, and in papers referenced therein. These papers describe the system for effecting carotid sinus nerve stimulation by a radio frequency responsive stimulator activated by the patient at will in response to the patient's awareness of the onset of angina and/or supraventricular tachycardia.

While these investigators focused upon the control of angina pectoris by regulation of the patient's blood pressure through stimulation of the carotid sinus nerve, they observed that the effect of the application of carotid sinus nerve stimulation provided a safe means for initiating reflex vagal activity which in turn effected a slowing in a patient's supraventricular tachycardia.

Thus, it is well known that the application of stimulation to the right or left vagus nerve, either directly or indirectly, has the effect of slowing tachycardias with the attendant possibility that a bradyarrhythmia may be induced in the process.

However, the difficulty in determining the proper amplitudes, frequencies and durations of the electrical stimulation indicated by Bilgutay et all coupled with continuing difficulty in the chronic vagal stimulation and other nerves has effectively led to the near abandonment of this therapy in recent years.

SUMMARY OF THE INVENTION

The present invention contemplates a method and apparatus for effecting vagal stimulation to both prevent or interrupt tachyarrhythmias and for applying pacing therapies to maintain the patient's heart rhythm within acceptable limits. It is thus an object of the present invention to prevent or interrupt tachyarrhythmias and to restore and maintain adequate cardiac function through stimulation of the vagal nerves as well as the heart tissue in a concerted fashion dependent upon need as automatically determined by the system.

More particularly, the present invention contemplates the detection of a tachycardia susceptible to correction by stimulation of the vagal nerves not only by comparison of the patient's heart rate to a preset tachycardia threshold rate or tachycardia detection interval but the examination of other criteria related to complex ventricular arrhythmias and changes in ST segment elevations suggesting acute myocardial ischemia.

Moreover, the method and apparatus of the present invention contemplates the inclusion of cardiac pacing with vagal stimulation initiated by detection of such indices in order to overcome bradyarrhythmias induced by the vagal stimulation and maintain an adequate cardiac output until the patient's heart exhibits normal sinus rhythm.

The method and apparatus of the present invention further includes providing memory capabilities for storing the patient's electrogram for a determined time interval preceding and following each instance that vagal stimulation is found necessary as well as other data associated with the detection of the aforementioned indices and the delivery of the stimulation therapy for later telemetry out on command and analysis by the physician.

The method and apparatus of the present invention is realized with tachyarrhythmia detection criteria which includes the detection of the heart rate as measured by the R—R intervals between a series of successive R-waves, the occurrence of frequent or complex ventricular arrhythmias, and a change in the ST segment elevation greater than a programmed threshold elevation suggesting acute myocardial ischemia in addition to ventricular tachycardia.

In order to develop the programmed thresholds, physician may exercise a patient on a treadmill and thereby induce ventricular tachycardia while measuring the heart rate, the ST segment elevation and the characteristics of complex ventricular arrhythmias that may be induced in the work up and electrophysiologic study. From the results of the work up and study, the physician may select programmable values for the rate and frequency detection criteria of ventricular tachyarrhythmias and the elevation threshold for the ST segment elevation characteristic of the threshold ventricular tachycardia that the physician desires to treat through stimulation of the vagal nerves. At the same time, the physician may examine the efficacy of vagal stimulation and set the characteristics of the vagal stimulation pulse trains accordingly.

Thus, the method and apparatus of the present invention contemplates the inclusion of therapies for stimulating both the patient's vagal nerves and the patient's heart and the recording in memory of the detection of the arrhythmia, the cardiac response to the vagal stimulation and the real time (date and time of day) that vagal stimulation was delivered.

BRIEF DESCRIPTION OF THE DRAWINGS

These and other additional objects and features of the present invention will become readily apparent when the same are set forth in greater detail in the accompanying detailed description of the preferred embodiments with reference being made to the drawings in which like reference numerals represent like or similar parts throughout and in which.

DETAILED DESCRIPTION OF THE PREFERRED EMBODIMENT OF THE INVENTION

Figure 1:
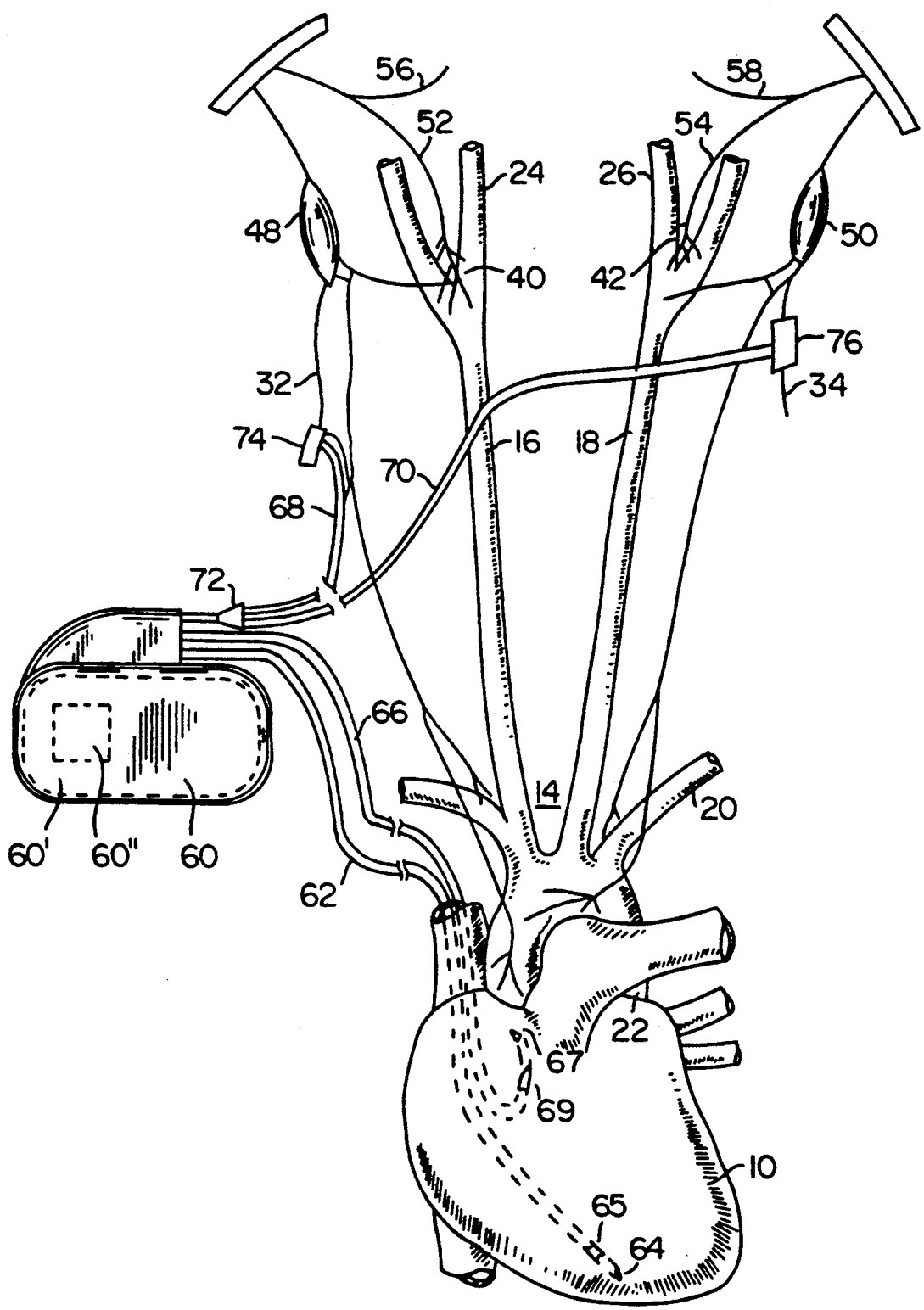
FIG. 1 is a diagrammatic illustration of the heart, its associated blood vessels and nerves, and the device of the present invention coupled thereto.

Before discussing the preferred embodiment of the present invention, it is helpful to briefly discuss the natural baroreceptor heart rate control system, which is shown in FIG. 1. The heart 10 pumps oxygenated blood out through the aortic arch 12, which leads to the right subclavian artery 14, the right common carotid 16, the left common carotid 18, the left subclavian artery 20, and the thoracic aorta 22. The body's system utilizes stretch receptors located in the arterial walls in the aortic arch 12 and at the bifurcation of the carotid arteries 16, 18 in the carotid sinus portion of the neck. The bifurcation of the carotid arteries 16, 18 leads to exterior carotid arteries 24, 26, respectively, and to interior carotid arteries 28, 30, respectively.

Nerve fibers extending from stretch receptors in the aortic arch 12 join the left and right vagus nerves 32, 34, respectively, with these fibers being referred to as cardiac depressor nerves 36, 38. A number of nerves extend from the stretch receptors at the bifurcation of the carotid arteries 16, 18 in the carotid sinus, with the areas immediately above the bifurcations being referred to as the carotid bodies 40, 42. Nerve branches 44, 46 extending from the carotid bodies 40, 42, respectively, join the ganglions of vagus 48, 50, respectively. Other nerve fibers comprising the sinus nerve branches 52, 54 (generally referred to as "Hering's nerves") of the glossopharyngeal nerves 56, 58, respectively, also extend from the carotid bodies 40, 42, respectively, to the medulla (not shown).

FIG. 1—Elements

10 Heart
12 aortic arch
14 right subclavian artery
16 right common carotid
18 left common carotid
20 left subclavian artery
22 thoracic artery
24 exterior carotid artery
26 exterior carotid artery
28 interior carotid artery
30 interior carotid artery
32 left vagus nerve
34 right vagus nerve
36 cardiac depressor nerve
38 cardiac depressor nerve
40 carotid body
42 carotid body
44 nerve branch of carotid body
46 nerve branch of carotid body
48 ganglions of vagus
50 ganglions of vagus
52 sinus nerve branch
54 sinus nerve branch
56 glossopharyngeal nerve
58 glossopharyngeal nerve
60 pulse generator
60' indifferent electrode
60" activity sensor
62 ventricular pace/sense lead
64 ventricular pace/tip electrode
65 ventricular pace/proximal electrode
66 atrial pace/sense lead
67 atrial tip electrode
69 atrial proximal electrode
68 nerve stimulating lead
70 nerve stimulating lead
72 incline connector adaptor
74 left vagus stimulating electrode
76 right vagus stimulating electrode The rate of the heart is restrained by the right and left vagus nerves 32,34, respectively in conjunction with the cardiac depressor nerves 36, 38, respectively. The cardio-inhibitory center of the nervous system exerts a tonic effect upon the heart, via the vagus nerves, restraining its rate. This effect is better known as vagal tone. The loss of vagal tone may be instrumental in triggering various arrhythmias including paroxysmal atrial tachycardias, premature atrial extra systoles, atrial fibrillation, tachycardia, etc. In either case, selective electrode stimulation of the right or left vagus nerve 32, 34 may, as taught by Bilgutay et all bring into control the tachycardias of ventricular or supraventricular nature without resorting to direct stimulation of the heart. With vagal stimulation, it is possible to slow the heart rate down and allow more complete relaxation and increased filling of the ventricles. Also, with relatively larger diastolic volumes, it is expected that the heart would beat more efficiently as less energy would be lost to overcome the myocardial viscosity and elastic forces of the heart with each beat. The right vagus nerve 34 is most frequently stimulated because its distribution is known to importantly involve the sinus node area of the heart.

As stated hereinbefore, the present invention also contemplates reliance upon the ST threshold elevation indicative of acute myocardial ischemia in triggering the stimulation of the vagal nerves. The stimulation of the vagal nerves under these circumstances acts indirectly on the carotid sinus nerves and reduces both blood pressure level as well as heart rate. This decreases myocardial workload and so reduces anginal pain. Vagal stimulation has a vasodilator effect, which contributes to lower blood pressure.

Returning to FIG. 1, the system depicted therein includes a bradyarrhythmia pacemaker, preferably a dual chamber rate responsive pacemaker of the type described in Medtronic U.S. Pat. No. 4,951,667, issued to Markowitz et al., and U.S. patent application Ser. No. 567,476, filed Aug. 14, 1990, in the name of Bennett et al., both incorporated herein by reference, together with a programmable nerve stimulator responsive to the aforementioned arrhythmias or to patient activation for applying nerve stimulating impulses to one or more electrodes. The pulse generator 60 is attached at its connector block to a ventricular lead 62 and atrial lead 66 as well as a left vagal nerve stimulating lead 68 and right vagal nerve stimulating lead 70. The ventricular pacing lead 62 includes a distal tip electrode 64 and proximal ring electrode 65 of the type commonly employed in pacing for sensing the R-waves of the patient's heart and delivering stimulating pulses to the ventricle. Similarly, the atrial pacing lead 66 is schematically shown extending through the patient's venous system, the superior vena cava and into the right atrium of the heart 10 in order to lodge distal tip electrode 67 and proximal ring electrode 69 in the atrial appendage in a fashion well known in the pacing art. The electrodes 67, 69 are employed for bipolar, near-field sensing of atrial depolarizations or P-waves and for the delivery of pacing pulses to the atrium.

The indifferent plate electrode 60' may be used in conjunction with the electrodes 67, 69 and 64, 65 to provide unipolar for field sensing or stimulation (as opposed to bipolar sensing or stimulation) in a manner well known in the pacing art. In the context of the present invention, the indifferent electrode 60' is especially employed in connection wit the ventricular tip electrode 64 to derive a unipolar or far field representation of the elevation of the ST segment of the PQRST depolarization wave form in a fashion to be described hereinafter.

A second pair of electrical leads 68 and 78 extend from an inline connector adaptor 72 from the connector block of the pulse generator 60 to the respective left and right vagus nerves 32, 34. The electrodes 74 and 76 are placed around the left and right vagus nerve bodies in a manner described, for example, in the aforementioned U.S. Pat. Nos. 3,421,511 and 3,522,811, and the aforementioned Bilgutay et all article, all incorporated herein by reference.

Figure 2:
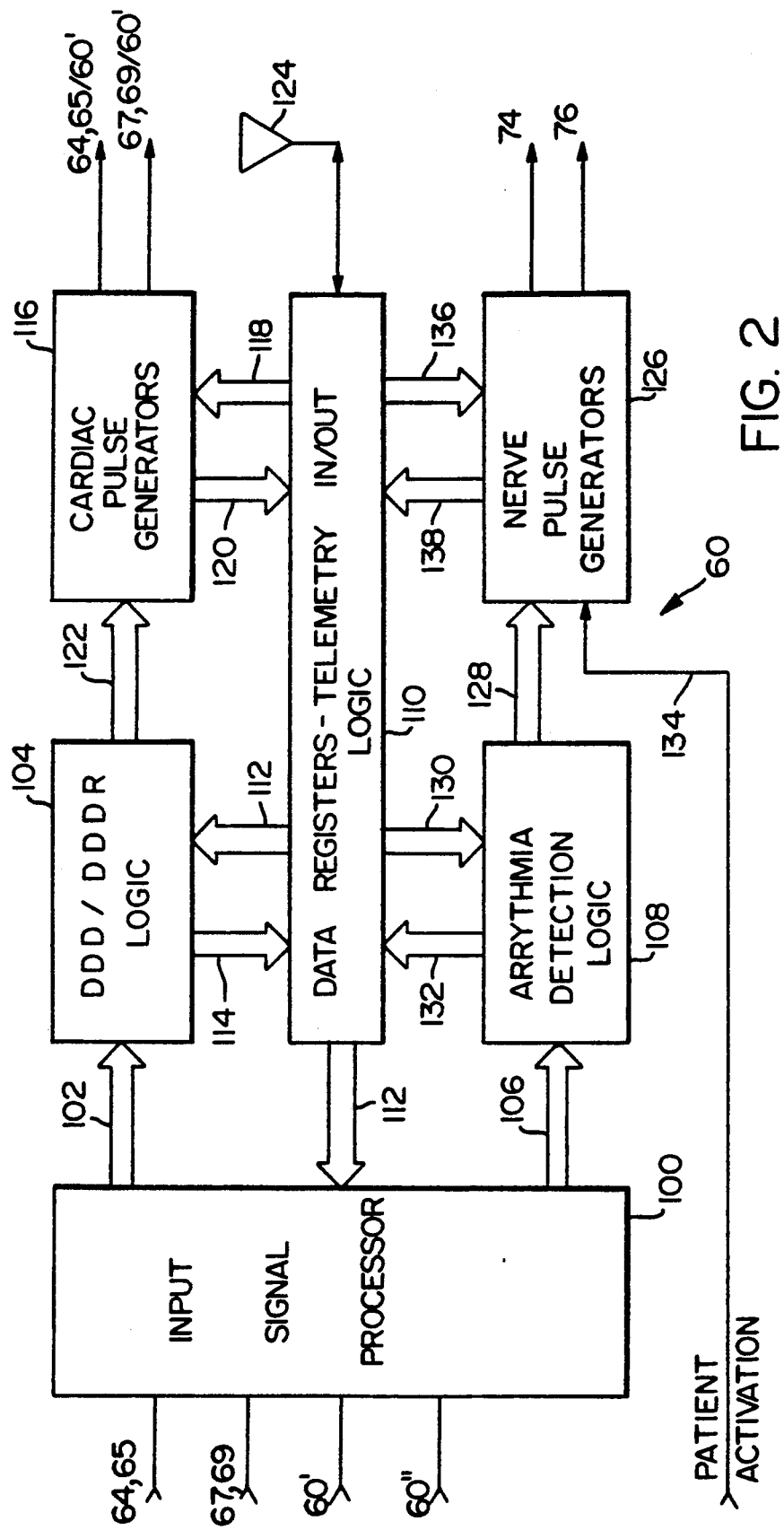
FIG. 2 is a block diagram of one form of electrical stimulator system that may be used in the practice of the invention.

Turning now to FIG. 2, an overall functional block diagram of the pacing and nerve stimulating system of the present invention is depicted. The system for detecting the onset of an arrhythmias amenable to control by stimulation of the vagal nerves is depicted more specifically in FIG. 3. The overall system of FIG. 2 comprises six blocks including an input signal processor for receiving input signals from the heart, the activity of the patient and a patient activation signal, decision logic blocks for triggering either the delivery of pacing stimuli, in the case of a bradyarrhythmia, or nerve stimuli, in the case of a tachyarrhythmia, and data registers and system control logic for effecting the storage of data associated with the detection and treatment of the tachyarrhythmia for telemetry out on command of an external transceiver and for controlling system operation as a function of programmed-in mode and parameter data. The external transceiver (not shown) may comprise a programmer with input/output telemetry such as a Medtronic Model 9710 pacemaker programmer with appropriate software. Preferably, the system depicted in FIG. 2 would be implemented in digital logic and/or microprocessor technology involving RAM and ROM data registers for storing mode and parameter data programmed into the device by the external programmer and for storing segments of electrocardiograms or ECG's on detection of a tachyarrhythmia as described hereinafter.

In FIG. 2, the input signal processor block 100 receives the bipolar ventricular ECG or R-wave from electrodes 64, 65, the bipolar atrial ECG or P-wave from atrial electrodes 67, 69, the far field ECG from indifferent electrode 60' (in conjunction with one or more of the aforementioned electrodes), and the signal from the activity sensor 60''. The input signal processor 100 includes digital logic and amplifier circuits for deriving a first set of data representative of the activity level of the patient and the atrial and ventricular ECG's or P-waves and R-waves, respectively, which are applied through data bus 102 to the DDD/DDDR logic block 104. The input signal processor 100 in addition processes the new field R-waves and the far-field electrogram to derive signals indicative of the elevation of the ST segment of the ECG, the occurrence of frequent or complex ventricular arrhythmias, and the elevation of the heart rate greater than a predetermined threshold indicative of a tachycardia, which signals are applied by data bus 106 to the arrhythmias detection logic 108. The input signal processor includes conventional DDD/DDDR pacemaker sense amplifiers and activity signal processors, the sensitivity of which may be adjusted under the command of the data register-telemetry in/out logic block 110 through data bus 112 in a manner well known in the pacing art. Similarly, blanking and refractory interval data commands may be applied to the sense amplifiers within the input signal processor block 100 through data bus 112 in a manner well known in the dual chamber pacing art.

The data registers-telemetry in/out logic block 110 is coupled to the DDD/DDDR logic block 104 by data buses 112 and 114 for applying programmed-in commands to the interval timing logic within block 104 in order to set the lower and upper rate pacing limits, the AV and VA timing intervals, the modes of operation (unipolar/bipolar, single chamber or dual chamber, etc.) of the pacemaker, and other functions of pacemakers of the type described in the aforementioned 567,476 patent application and '667 patent. Data derived from the DDD/DDDR logic block 104 is transmitted back to the data registers within the data registers-telemetry in/out logic block 110 on bus 114.

Data registers-telemetry in/out logic block 110 is also coupled to the atrial and ventricular cardiac pulse generators block 116 by data buses 118 and 120. The cardiac pulse generators block 116 also receive stimulating pulse generation commands from the DDD/DDDR logic block 104 over bus 122 and deliver atrial and/or ventricular stimulation impulses to atrial electrodes 64, 65 or 60' and 67, 69 or 60' electrodes, respectively. The energy of the stimulating pulses delivered to the patient's heart by cardiac pulse generators 116 may be controlled by data programmed into the data registers-telemetry in/out logic 110 and applied to the pulse generator circuitry through bus 118. Data associated with the deliverable energy of the power source supplying the power or the system as a whole and/or the cardiac pulse generators and data related to the integrity of the lead and electrode system may be applied back to the data registers-telemetry in/out logic 110 over bus 120. The runaway prevention lower rate and upper rate limit control signals may also be applied by data registers-telemetry in/out logic 110 through bus 118 to the cardiac pulse generator 116 all in a manner well known in the pacing art. The cardiac pulse generators 116 are the type disclosed in the aforementioned 567,476 patent application and '667 patent.

The data registers-telemetry in/out logic 110 is also coupled to a telemetry antennae 124 for receiving and transmitting programming and telemetry data to the aforementioned external transceiver or programmer in a manner well known in the pacing art.

Figure 3:
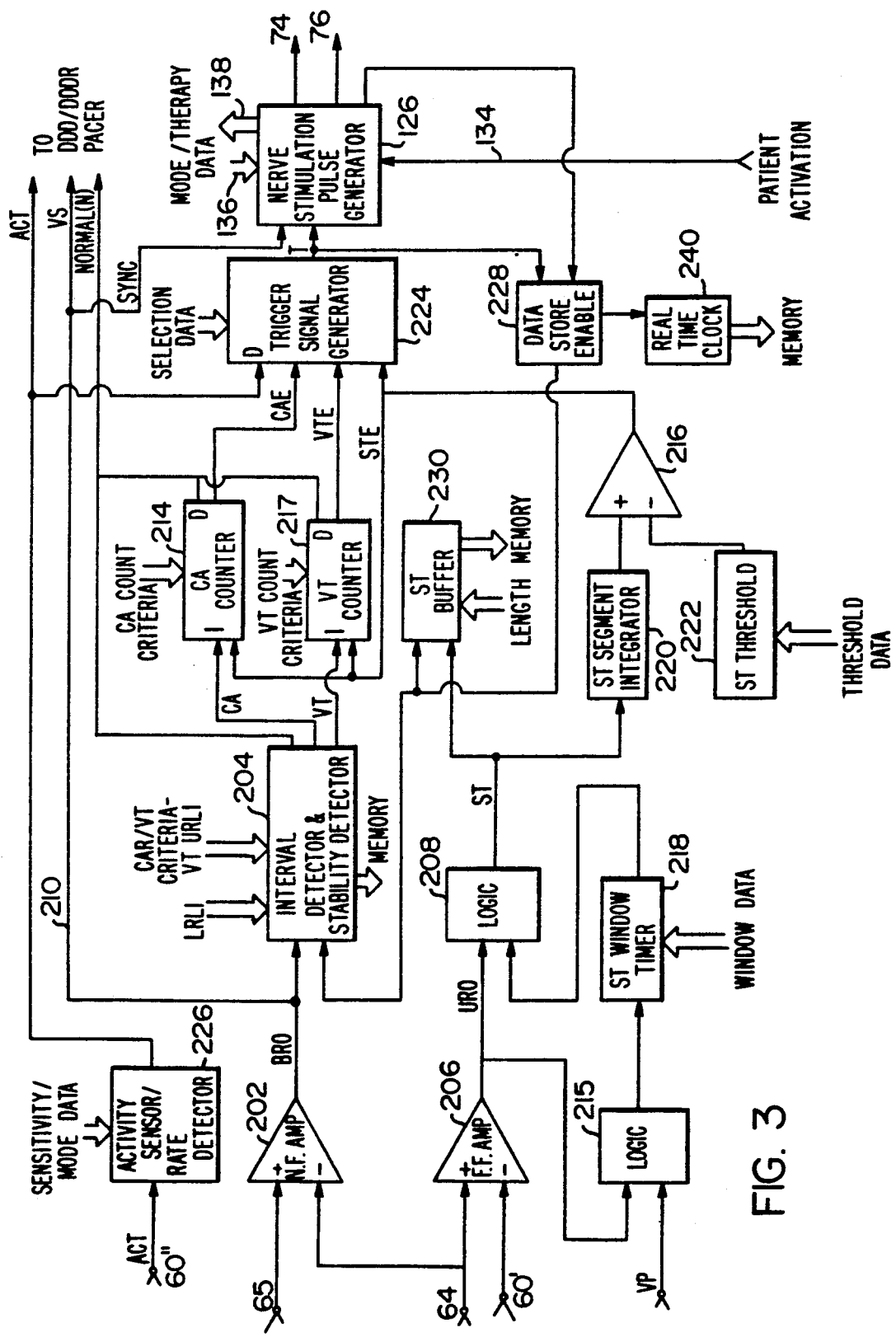
FIG. 3 is a circuit diagram of the detection circuitry for detecting the arrhythmias for triggering vagal stimulation in accordance with the invention.

The arrhythmias detection logic 108 includes circuitry for providing nerve stimulation command signals to the nerve pulse generators block 126 by way of data bus 128 in a manner to be described in reference to FIG. 3. The arrhythmias detection logic 108 is coupled by an input data bus 130 and an output data bus 132 to the data registers-telemetry in/out logic block 110 to provide for the control of the arrhythmias detection logic by data stored in the data registers within block 110 and to provide for the storage of specific data within data registers of block 110 upon detection of a specific arrhythmias in a manner to be described in reference to FIG. 3.

The nerve pulse generators 126 receive a further input labeled patient activation on line 134 to provide for a patient override in the event that the patient feels the onset of an arrhythmia or an anginal episode that apparently is being untreated or inadequately treated by the nerve pulse generators 126. The patient activation may involve the provision to the patient of a special limited capability transmitter or a magnet for closing a reed switch. It will be understood that in the event the patient activation system is a limited capability transmitter, then it would act through the telemetry in/out antennae 124 and logic block 110 rather than through a separate line as depicted in FIG. 2.

In regard to the interface between the data registers-telemetry in/out logic 110 and the nerve pulse generators block 126, data for controlling the mode and parameters of the stimulating impulses to be delivered by the nerve pulse generators block 126 to the nerve stimulating electrodes 74, 76 is applied by way of bus 136. Such parameter data may include the frequency and amplitude of stimulating pulses to be delivered in a burst of such pulses to one or both of the electrodes 74, 76. In addition, the number of bursts in a single therapy provided in response to a single tachyarrhythmia detect event may be also programmed into the system and stored in data registers within logic block 110. As in the case of the cardiac pulse generators block 116, data relating to the available energy of the power source supplying the nerve pulse generators and the integrity of the lead and electrode system may be stored in dedicated data registers of logic block 110 through data bus 138.

The overall system depicted in FIG. 2 is intended to provide for the automatic detection of the need for vagal stimulation in response to increases in heart rate greater than a predetermined threshold, the occurrence of frequent or complex ventricular arrhythmias and/or a change in the ST segment elevation greater than a predetermined or programmed threshold. The stimulation of the right or left vagal nerve with continuous and/or phasic electrical pulses, the latter in a specific relationship with the R-wave of the patient's electrogram, is preferably highly flexible so as to allow a broad range of stimulating energies and frequencies, burst durations, intervals between bursts and numbers of bursts in a given therapy all under the control of the physician employing the external programmer and the data registers within the data registers of logic block 110. In addition, the system is designed to record in memory data relating to the detection of the need for vagal stimulation, including the actual QRST electrocardiogram associated with the detection of the occurrence of frequent or complex ventricular arrhythmias, the tachycardia and/or the change in ST segment elevation, as well as the date and time of day so that the physician can diagnose the patient's particular pattern of experiencing symptoms.

Returning to the vagal stimulation therapies, the nerve stimulation pulse generators block 126 applies a programmed therapy regimen of one or more nerve stimulating impulses to one or both of the electrodes 74, 76 under the control of the logic block 110 and in response to trigger signals developed by a programmable trigger signal generator within block 108 which may respond to an R-wave synchronization trigger/delay signal and an activity signal generated by block 100. The arrhythmia detection logic block 108 is thus programmable to provide synchronization with an R-wave or to ignore synchronization with an R-wave. If synchronization is programmed on, then the burst trigger signal generator within block 108 is started after a further programmable delay from the R-wave signal employed as the synchronization signal.

The memory and logic within block 110 may provide a programmable number of stimulating pulses to be applied in a burst of such pulses, the number of bursts of pulses within a single therapy, the pulse width of each individual stimulating pulse, the intervals between individual stimulating pulses, the intervals between bursts of pulses in a given therapy, the scanning of the intervals between pulses within a given burst or between successive bursts or both and the number of therapies to be delivered on the detection of a single ventricular tachyarrhythmia. Moreover, the output electrodes 74 and 76 may be enabled selectively under the control of the block 110 so that pulse therapies may be applied alternately to the electrodes 74 and 76.

In the context of the present invention, it will be understood that the detection of symptoms of a tachyarrhythmia amenable to vagal stimulation, the application of vagal stimulation therapy regimens and the storage of data pertaining to the detection of a tachyarrhythmia treated by vagal stimulation and the resulting electrogram of the heart following the delivery of therapies is essential to the present invention. It is contemplated that up to five minutes of successive R—R intervals preceding the detection of the tachycardia and following the delivery of nerve stimulation therapies may be stored in memory for subsequent telemetry out on command of an external programmer/receiver.

Turning now to FIG. 3, the ventricular signal portion of the input signal processor 100, the arrhythmia detection logic block 108, and the nerve pulse generators block 126 are shown in greater detail. In FIG. 3, the near field and far field ventricular electrograms are employed to develop the R—R intervals between successive R-waves to detect ventricular tachycardia, to determine the frequency of occurrences of complex arrhythmias and to detect elevated ST segments in a predetermined ST time window. If ST segments are elevated, the elevated ST segment data in conjunction with the aforementioned data is employed as indices sufficient to trigger the delivery of a nerve stimulation therapy.

The circuit of FIG. 3 employs the near field and far field electrograms derived respectively from the bipolar electrodes 64 and 65 and the case electrode 60' of the pulse generator 60 of FIG. 1 and develops the BRO, URO, VS, N, CA, ST, VT, CAE, VTE and STE signals shown at various points in the circuit. The circuit of FIG. 3 also receives and transfers data on the data buses to and from logic block 110 of FIG. 2 for applying detection criteria and mode and therapy data to blocks within FIG. 3 and for receiving into memory detected data as described hereinafter. The transmission of data to and from the logic block 110 is depicted as labeled buses entering or leaving blocks of FIG. 3.

In FIG. 3, the bipolar electrogram is detected by the near field sense amplifier 202 to develop the bipolar R-out (BRO) signal that is applied to the input of the interval and stability detector 204. At the same time, the unipolar electrogram is received across 64 and 60' and applied to the far field sense amplifier 206 which develops the unipolar R-out (URO) signal which in turn in applied to one input of gate 208. The BRO signal is also applied to line 210 as the signal VS which is employed by DDD/DDDR logic and timing block 104 of FIG. 2.

The existence of a ventricular tachycardia (VT) or complex arrhythmias (CA) is determined by the interval and stability detector 204 in conjunction with the VT counter 212 and the CA counter 214. Very generally, the tachycardia detection system of the present invention employs the rate discrimination between VT and normal sinus rhythm (N) by comparing each R—R interval against a programmed threshold interval (corresponding, for example, to an upper rate limit) and concluding in block 212 that VT is present if a programmed number of such intervals are shorter than the threshold interval. If a ventricular tachycardia condition is found to exist, then the preferred therapy is to apply vagal stimulation as described hereinbefore.

Similarly, employing complex arrhythmia criteria programmed into the interval detector and stability detector block 204 and count criteria programmed into the counter 214, the blocks 204 and 214 detect the frequency of complex arrhythmias occurring within a series of successive R to R intervals or over a period of time. If a programmed number of complex arrhythmias are detected within a programmed number of R to R intervals or a programmed period of time, then the counter 214 develops the complex arrhythmia enable signal CAE. The count of counters 212 and 214 are incremented by the signals CA and VT which satisfy the complex arrhythmia and ventricular tachycardia detection criteria of block 204. Similarly, the counts of counters 212 and 214 may be decremented by the detection of normal sinus rhythm (N).

The rate discrimination may further include rate stability and sudden onset criteria discrimination at block 204 to discriminate between exercise induced or pathologic VT in a manner well known in the prior art. In addition, block 204 may be employed to record the frequency of recurring tachyarrhythmia events over a given period of time as determined by data from the block 110 and to transfer that number to a memory within block 110. Appropriate discrimination circuitry and algorithms for discriminating between sinus tachycardia and malignant ventricular tachycardia and ventricular fibrillation are set forth in U.S. Pat. No. 4,548,209, issued Wielders et al., incorporated herein by reference.

Turning now to the ST segment elevation detection and discrimination, the URO signal is applied to one input terminal of gate 215 which receives at its second input signal the ventricular pace or VP signal. Gate 215 acts as an OR gate to transfer either signal to the ST window timer block 218 which sets up window of time following either a URO or VP signal. That window signal is applied as a second input to gate 208 which acts as an AND gate with the signal URO to provide only the ST segment (and to exclude the PQRS complex) to the input of the integrator 220 and the ST segment buffer 230. The ST segments applied to the ST segment buffer 230 are stored in a FIFO fashion for a length of time determined by data from block 172. When triggered by detection of an elevated ST segment, the contents of the ST buffer are transferred to memory within the block 110.

The ST segment applied to the input of the integrator 220 is integrated to present a ST segment value to the first input of differential amplifier 216. The second input of differential amplifier 216 is coupled to the ST threshold value block 222 into which threshold data programmed into memory in block 110 is transferred. It is anticipated that all of the data applied by input buses to the blocks of FIG. 3 may be programmed into data memory of block 110 in the fashion mentioned hereinbefore.

When the integrated ST segment value applied to the positive input terminal of amplifier 216 exceeds the ST threshold value in block 222, then an STE signal is developed which is applied to AND/OR logic block 224 and to further inputs of VT and CA counters.

Very generally speaking, the STE signal is applied to the counters 212 and 214 as well as the logic block 224 so that the elevated ST segment signal may either increment the counters to accelerate the satisfaction of the count criteria and/or to enable the logic block 224 to provide a trigger signal at its output that is applied as an input to the nerve stimulation pulse generator 126. It is contemplated that the STE signal may be used or not used in the counters 212 and 214 in accordance with the count criteria data applied thereto and will be used principally in the logic block 224 as a primary selection criteria for the triggering of the nerve stimulation pulse generator 126. Each of the signals CAE, VTE and STE may be selectively used in combination or separately in accordance with selection data applied to logic block 224 from data registers in logic block 110 to generate the burst stimulation trigger signals to be applied to the nerve stimulation pulse generator 126.

The logic block 224 has a further input labeled D which receives the activity signal in ACT developed by the activity sensor/rate detector block 226. The activity sensor/rate detector 226 manipulates activity data from the activity sensor 60" in conjunction with sensitivity and mode data applied thereto by logic 110 to provide an activity signal ACT representing the degree to which the patient is resting or exercising. An ACT signal of a certain magnitude indicative of patient exercise is applied to the input D of logic block 224 to disable the generation of a nerve stimulation pulse trigger signal in those instances where a patient, exercising normally and asymptomatically, nevertheless develops an elevated ST segment or otherwise satisfies the detection criteria that would satisfy the programmed criteria and selection data to enable vagal nerve stimulation. It is expected that this activity data input may be programmed in or out of consideration by the programmed-in selection data.

As an additional feature of the present invention, the patient's selection trigger input on line 134 is provided to allow the patient to override the detection criteria in the manner described hereinbefore in reference to FIG. 2.

A feature of the present invention involves the storage of data associated with the detection of the elevated ST segments, ventricular tachycardia and complex arrhythmias as well as the date and time of day of the detected symptoms. In FIG. 3, the data store enable block 228 is activated by both the satisfaction of the logic block 224 selection criteria as well as the completion of the delivery of the nerve stimulation therapy by the nerve stimulation pulse generator block 126. Thus, upon satisfaction of the detection criteria, a predetermined number of ST segments in FIFO ST buffer 230 may be transferred to memory. Similarly, measured R to R intervals may also be transferred to memory from block 204.

Thus, the logic of FIG. 3 may employ the bipolar electrogram rate and frequency of occurrence related signals as well as the elevated ST segment signal to provide an output signal indicative of VT to the remaining components of FIG. 2. It will be understood that the circuit depicted in FIG. 3 is merely illustrative of digital logic circuitry which may be employed in the discrimination between normal and abnormal heart rhythms including brady and tachyarrhythmias as described hereinbefore.

Although not specifically described, the system may further include a patient-initiated storage of the aforementioned physiological conditions and treatment by delivery of stimulation. Failure of stimulation to prevent recurrences within a programmable period of time after detection of each episode may also be stored in memory and used to trigger an increase in stimulation amplitude and/or duration. Stimulation frequency may be varied in a predetermined pattern from the optimum stimulation frequency, amplitude and duration determined during patient work up, if the initially-delivered therapy fails to convert the tachyarrhythmia. Successful therapy regimens may be stored in memory and used as the starting therapy when the tachyarrhythmia recurs.

Thus the present invention contemplates the automatic detection of the need for vagal stimulation in response to increases in heart rate greater than a predetermined tachycardia threshold and the change in ST segment elevation indicative of an elevated heart rate and/or myocardial ischemia. It will be understood that the present invention may be employed with other indicators of ventricular tachycardias than those specifically described herein.

What is claimed is:

1. A method for treating a cardiac arrhythmia comprising the steps of:
   continuously measuring the electrogram of the patient's heart;
   detecting certain characteristics of said electrogram indicative of tachycardia;
   initiating the storage of a sequence of said characteristics of said electrogram upon detection of a tachycardia;
   delivering one or more electrical stimulation therapies to the patient's nervous system for depressing the patient's heart rate;
   providing a patient selection trigger to permit a patient to cause the delivery of a preset electrical stimulation therapy to the patient's nervous system;
   providing patient initiated storage means to permit the patient to initiate storage of said sequence of said characteristics of said electrogram and said delivering of said one or more electrical stimulation therapies to the patient's nervous system for depressing the patient's heart rate; and
   initiating the storage of a further sequence of said characteristics of said electrogram following delivery of said stimulation therapies.

2. The method of claim 1 further comprising the steps of:
   examining the QRST segment of the patient's electrogram;
   measuring the ST segment elevation of said QRST components of said electrogram;
   comparing the measured ST segment elevations to a threshold ST segment elevation and counting the number of elevated ST segments exceeding the threshold ST segment elevation; and
   delivering said stimulation therapies if a pre-selected number of elevated ST segments among a total number of measured ST segments are found.

3. The method of claims 1 or 2 further comprising the steps of:
   detecting successive R-waves of the patient's electrogram;
   measuring successive R—R intervals of the patient's electrogram and comparing the measured R—R intervals against a tachycardia interval threshold; and
   delivering said stimulation therapies if a predetermined number of R—R intervals within a run of successive R-waves are less than said tachycardia threshold interval.

4. The method of claim 1 wherein said step of storing the electrogram after delivery of stimulation further comprises the steps of:
   confirming that the delivered stimulation therapy successively converted the tachycardia to a heart rate below the tachycardia threshold; and
   storing a predetermined number of successive R—R intervals following delivery of a successful therapy.

5. Apparatus for treating a cardiac arrhythmia comprising:
   means for continuously measuring the electrogram of the patient's heart;
   means for detecting certain characteristics of said electrogram indicative of tachycardia;

means for a sequence of said characteristics of said electrogram upon detection of tachycardia;

means for delivering one or more electrical stimulation therapies to the patient's nervous system for depressing the patient's heart rate;

patient selection trigger means for permitting a patient to cause the delivery of a preset electrical stimulation therapy to the patient's nervous system;

patient initiated storage means for permitting the patient to initiate storage of said sequence of said characteristics of said electrogram and said delivering of said one or more electrical stimulation therapies to the patient's nervous system for depressing the patient's heart rate; and means for storing of a further sequence of said characteristics of said electrogram following delivery of said stimulation therapies.

6. The apparatus of claim 5 further comprising:

means for examining the QRST segment of the patient's electrogram;

means for measuring the ST segment elevation of said QRST components of said electrogram;

means for comparing the measured ST segment elevations to a threshold ST segment elevation and means for counting the number of elevated ST segments exceeding the threshold ST segment elevation; and means for delivering said stimulation therapies if a preselected number of elevated ST segments among a total number of measured ST segments are found.

7. The apparatus of claims 5 or 6 further comprising:

means for detecting successive R-waves of the patient's electrogram;

means for measuring successive R—R intervals of the patient's electrogram and comparing the measured R—R intervals against a tachycardia interval threshold; and means for delivering said stimulation therapies if a predetermined number of R—R intervals within a run of successive R-waves are less than said tachycardia threshold interval.

8. The apparatus of claim 5 wherein said step of storing the electrogram after delivery of stimulation further comprises:

means for confirming that the delivered stimulation therapy successively converted the tachycardia to a heart rate below the tachycardia threshold; and means for storing a predetermined number of successive R—R intervals following delivery of a successful therapy.

9. A method for treating a cardiac arrhythmia comprising the steps of:

continuously measuring the electrogram of the patient's heart;

examining the QRST segment of the patient's electrogram;

measuring the ST segment elevation of said QRST components of said electrogram;

comparing the measured ST segment elevation to a threshold ST segment elevation and counting the number of elevated ST segments exceeding the threshold ST segment elevation; and delivering one or more electrical stimulation therapies to the patient's nervous system for depressing the patient's heart rate;

providing a patient selection trigger to permit a patient to cause the delivery of a preset electrical stimulation therapy to the patient's nervous system; and providing patient initiated storage means to permit the patient to initiate storage of said sequence of said characteristics of said electrogram and said delivering of said one or more electrical stimulation therapies to the patient's nervous system for depressing the patient's heart rate.

10. The method of claim 9 further comprising the steps of:

detecting successive R-waves of the patient's electrogram;

measuring successive R—R intervals of the patient's electrogram and comparing the measured R—R intervals against a tachycardia interval threshold; and delivering said stimulation therapies if a predetermined number of R—R intervals within a run of successive R-waves are less than said tachycardia threshold interval.

* * * * *